United States Patent
Tsai et al.

(10) Patent No.: US 8,062,873 B2
(45) Date of Patent: Nov. 22, 2011

(54) HORIZONTAL ARRAY BIOREACTOR FOR CONVERSION OF SYNGAS COMPONENTS TO LIQUID PRODUCTS

(75) Inventors: Shih-Perng Tsai, Naperville, IL (US); Rathin Datta, Chicago, IL (US); Rahul Basu, Naperville, IL (US); Seong-Hoon Yoon, Naperville, IL (US)

(73) Assignee: Coskata Energy, Warrenville, IL (US)

( * ) Notice: Subject to any disclaimer, the term of this patent is extended or adjusted under 35 U.S.C. 154(b) by 558 days.

(21) Appl. No.: 12/258,162

(22) Filed: Oct. 24, 2008

(65) Prior Publication Data
US 2009/0215142 A1 Aug. 27, 2009

(51) Int. Cl.
C12M 1/12 (2006.01)
C12M 1/14 (2006.01)
C12P 1/04 (2006.01)

(52) U.S. Cl. ........ 435/170; 435/41; 435/165; 435/286.6; 435/297.4; 435/400

(58) Field of Classification Search .................... 435/41, 435/165, 170, 286.6, 297.4, 400
See application file for complete search history.

(56) References Cited

U.S. PATENT DOCUMENTS

| | | | |
|---|---|---|---|
| 4,181,604 A | 1/1980 | Onishi et al. | |
| 4,442,206 A | 4/1984 | Michaels et al. | |
| 4,746,435 A | 5/1988 | Onishi et al. | |
| 5,116,506 A | 5/1992 | Williamson et al. | |
| 5,173,429 A | 12/1992 | Gaddy et al. | |
| 5,753,474 A | 5/1998 | Ramey | |
| 6,043,392 A | 3/2000 | Holtzapple et al. | |
| 6,136,577 A | 10/2000 | Gaddy | |
| 6,340,581 B1 | 1/2002 | Gaddy | |
| 6,387,262 B1 | 5/2002 | Rittmann et al. | |
| 6,558,549 B2 | 5/2003 | Cote et al. | |
| 6,908,547 B2 | 6/2005 | Cote et al. | |
| 6,919,488 B2 | 7/2005 | Melnichuk et al. | |
| 7,118,672 B2 | 10/2006 | Husain et al. | |
| 7,169,295 B2 | 1/2007 | Husain et al. | |
| 7,189,323 B2 | 3/2007 | Lofqvist et al. | |
| 7,285,402 B2 | 10/2007 | Gaddy et al. | |
| 2005/0054087 A1 | 3/2005 | Cote et al. | |
| 2006/0021936 A1 | 2/2006 | Husain et al. | |
| 2006/0037896 A1 | 2/2006 | Cote et al. | |
| 2006/0163157 A1 | 7/2006 | Cote et al. | |
| 2008/0305539 A1 | 12/2008 | Hickey et al. | |
| 2008/0305540 A1 | 12/2008 | Hickey et al. | |
| 2009/0035848 A1 | 2/2009 | Hickey et al. | |
| 2009/0104676 A1 | 4/2009 | Tsai et al. | |
| 2009/0215139 A1 | 8/2009 | Datta et al. | |

FOREIGN PATENT DOCUMENTS

WO WO0208438 A2 1/2002
WO WO2008154301 12/2008

OTHER PUBLICATIONS

U.S. Appl. No. 12/258,193, filed Oct. 24, 2008, Datta et al.
Clausen, E.C., et al., "Ethanol From Biomass by Gasification/Fermentation", Presented at Plastics, Tires, Auto Wastes/Biomass MSW Symposium, Fall 1993, Chicago, 38 (3).
Klasson, K.T., et al., "Biological Production of Liquid and Gaseous Fuels from Synthesis Gas," Appl. Biochem.. Biotechnol., vol. 24-25, No. 1, Mar. 1990, 857-873.
Vega, J. L., et al., "The Biological Production of Ethanol from Synthesis Gas," Appl. Biochem. Biotechnol. vol. 20-21, No. 1, Jan. 1989, 781-797.
Phillips, John R., et al., "Synthesis Gas as Substrate for the Biological Production of Fuels and Chemicals," Appl. Biochem. Biotechnol. vol. 45-46, No. 1, Mar. 1994, 145-157.
Barik, S., et al., "Biological Production of Alcohols from Coal Through Indirect Liquefaction," Appl. Biochem. Biotechnol. vol. 18, No. 1, Aug. 1988, 363-387.
U.S. Appl. No. 11/441,392, filed May 25, 2006, Tanner et al.
U.S. Appl. No. 11/514,385, filed Aug. 31, 2006, Hickey
U.S. Appl. No. 12/036,007, filed Feb. 22, 2008, Tsai et al.
U.S. Appl. No. 12/258,180, filed Oct. 24, 2008, Tsai et al.
U.S. Appl. No. 12/123,249, filed May 19, 2008, Hickey et al.
U.S. Appl. No. 12/111,734, filed Apr. 29, 2008, Tsai et al.
Popular Mechanics, Coskata Ethanol Technology—How it Works—Illustration and Analysis, http://www.popularmechanics.com/science/research/4248759.html?series=19, Feb. 22, 2008, pp. 1-3.
Ethanol Production by *Saccharomyces cerevisiae* Immobilized in Hollow-Fiber Membrane Bioreactors, Douglas S. Inloes, et al., Applied and Environmental Microbiology, Jul. 1983, pp. 264-278, vol. 46. No. 1.
"Evidence for Production of n-Butanol from Carbon Monoxide by Butyribacterium methylotrophicum," Journal of Fermentation and Bioengineering, vol. 72, 1991, p. 58-60.
"Production of butanol and ethanol from synthesis gas via fermentation," Fuel, vol. 70, May 1991, p. 615-619.
Das, A. and L.G. Ljungdahl, Electron Transport Systems in Acetogens, Chapter 14, in Biochemistry and Physiology of Anaerobic Bacteria, L.G. Ljungdahl et al eds., Springer (2003).

(Continued)

*Primary Examiner* — Herbert J Lilling

(57) ABSTRACT

A membrane supported bioreactor arrangement and method for anaerobic conversion of gas into liquid products including membrane modules having hollow fibers, each of the hollow fibers formed from an asymmetric membrane wall having a porous outer layer defining biopores for retaining a porous biolayer about the outer surface of the membrane wall and a less permeable hydration layer around the hollow fiber lumen; a membrane vessel for retaining the membrane modules in a process gas for formation of the biolayer on the outer surface of the hollow fiber wall by interaction of microorganisms with a process gas and for the production of a liquid product, wherein the membrane vessel retains the membrane modules in a common horizontal plane; provides a seal between contents of the membrane tank and ambient atmosphere; and includes a liquid supply conduit for communicating the process liquid with the hollow fiber lumens of the hollow fibers.

4 Claims, 10 Drawing Sheets

OTHER PUBLICATIONS

Drake, H.L. and K. Kusel, Diverse Physiologic Potential of Acetogens, Chapter 13, in Biochemistry and Physiology of Anaerobic Bacteria, L.G. Ljungdahl et al eds., Springer (2003).

Muller, V., Minireview: Energy Conservation in Acetogenic Bacteria, Applied and Environmental Microbiology, vol. 69, 11, 6345-53, Nov. 2003.

Innovations in Wastewater Treatment: The moving bed biofilm process. Water Science and Technology vol. 53 No. 9 pp. 17-33, Publication date 2006.

Rahtin Datta and J.G. Zeikus, Anaerobic Conversion of One-Carbon Compounds. vol. 24 of Developments in Industrial Microbiology, 1983.

Datta et al, Reprinted from vol. 24 of Developments in Industrial Microbilogy, a Publication of the Society for Industrial Microbiology—1985, Chapter 10, Anaerobic Bioconversion of One-Carbon Compounds, pp. 1-6.

Kim et al, Plant Cell Immobilization in a Dual Hollow Fiber Bioreactor, Biotechnology Techniques vol. 3 No. 2, 1989, pp. 139-144, Received as revised Jan. 30.

Inloes, D. S, et al, Hollow-Fiber Membrane Bioreactors Using Immobilized *E. coli* for Protein Synthesis, pp. 2653-2681, Publication date 1983.

Nloes, D. S. et al, Ethanol Production by *Saccharomyces cerevisiae* Immobilized in Hollow-Fiber Membrane Bioreactors, Received Apr. 11, 1983/Accepted Apr. 25, 1983, Applied and Environmental Microbiology, Jul. 1983, vol. 46. No. 1, pp. 264-278.

Henstra, A. M. et al, Microbiology of Synthesis Gas Fermentation for Biofuel Production, ScienceDirect, Current Opinion in Biotechnology 2007, 18:200-206.

HORIZONTAL ARRAY BIOREACTOR FOR CONVERSION OF SYNGAS COMPONENTS TO LIQUID PRODUCTS

CROSS REFERENCE TO RELATED APPLICATIONS

This application claims priority from U.S. patent application Ser. No. 12/036,007, filed Feb. 22, 2008, incorporated herein in its entirety by reference.

FIELD OF THE INVENTION

This invention relates to the conversion of gas streams into liquid products using conversion modules that define separate gas and liquid contacting surfaces.

DETAILED DESCRIPTION

Background

Biofuels production for use as liquid motor fuels or for blending with conventional gasoline or diesel motor fuels is increasing worldwide. Such biofuels include, for example, ethanol and n-butanol. One of the major drivers for biofuels is their derivation from renewable resources by fermentation and bioprocess technology. Conventionally, biofuels are made from readily fermentable carbohydrates such as sugars and starches. For example, the two primary agricultural crops that are used for conventional bioethanol production are sugarcane (Brazil and other tropical countries) and corn or maize (U.S. and other temperate countries). The availability of agricultural feedstocks that provide readily fermentable carbohydrates is limited because of competition with food and feed production, arable land usage, water availability, and other factors. Consequently, lignocellulosic feedstocks such as forest residues, trees from plantations, straws, grasses and other agricultural residues may become viable feedstocks for biofuel production. However, the very heterogeneous nature of lignocellulosic materials that enables them to provide the mechanical support structure of the plants and trees makes them inherently recalcitrant to bioconversion. Also, these materials predominantly contain three separate classes of components as building blocks: cellulose ($C_6$ sugar polymers), hemicellulose (various $C_5$ and $C_6$ sugar polymers), and lignin (aromatic and ether linked hetero polymers).

For example, breaking down these recalcitrant structures to provide fermentable sugars for bioconversion to ethanol typically requires pretreatment steps together with chemical/enzymatic hydrolysis. Furthermore, conventional yeasts are unable to ferment the $C_5$ sugars to ethanol and lignin components are completely unfermentable by such organisms. Often lignin accounts for 25 to 30% of the mass content and 35 to 45% of the chemical energy content of lignocellulosic biomass. For all of these reasons, processes based on a pretreatment/hydrolysis/fermentation path for conversion of lignocellulose biomass to ethanol, for example, are inherently difficult and often uneconomical multi-step and multi conversion processes.

An alternative technology path is to convert lignocellulosic biomass to syngas (also known as synthesis gas, primarily a mix of CO, $H_2$, and $CO_2$ with other components such as $CH_4$, $N_2$, $NH_3$, $H_2S$, and other trace gases) and then ferment this gas with anaerobic microorganisms to produce biofuels such as ethanol, n-butanol or chemicals such as acetic acid, butyric acid and the like. This path can be inherently more efficient than the pretreatment/hydrolysis/fermentation path because the gasification step can convert all of the components to syngas with good efficiency (e.g., greater than 75%), and some strains of anaerobic microorganisms can convert syngas to ethanol, n-butanol or other chemicals with high (e.g., greater than 90% of theoretical) efficiency. Moreover, syngas can be made from many other carbonaceous feedstocks such as natural gas, reformed gas, peat, petroleum coke, coal, solid waste, and land fill gas, making this a more universal technology path.

However, this technology path requires that the syngas components CO and $H_2$ be efficiently and economically dissolved in the aqueous medium and transferred to anaerobic microorganisms that convert them to the desired products. And very large quantities of these gases are required. For example, the theoretical equations for CO or $H_2$ to ethanol are:

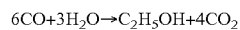

$$6CO + 3H_2O \rightarrow C_2H_5OH + 4CO_2$$

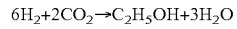

$$6H_2 + 2CO_2 \rightarrow C_2H_5OH + 3H_2O$$

Thus 6 moles of relatively insoluble gases such as CO or $H_2$ have to transfer to an aqueous medium for each mole of ethanol. Other products such as acetic acid and n-butanol have similar large stoichiometric requirements for the gases.

Furthermore, the anaerobic microorganisms that bring about these bioconversions generate very little metabolic energy from these bioconversions. Consequently they grow very slowly and often continue the conversions during the non-growth phase of their life cycle to gain metabolic energy for their maintenance. To get high yields and production rates the cell concentrations in the bioreactor need to be high and this requires some form of cell recycle or retention.

Many devices and equipment are used for gas transfer to microorganisms in fermentation and waste treatment applications. These numerous bioreactors all suffer from various drawbacks. In most of these conventional bioreactors and systems, agitators with specialized blades or configurations are used. In some others such as gas lift or fluidized beds, liquids or gases are circulated via contacting devices. The agitated vessels require a lot of mechanical power often in the range of 4 to 10 KW per 1000 gallons—uneconomical and unwieldy for large scale fermentations that will be required for such syngas bioconversions. The fluidized or fluid circulating systems cannot provide the required gas dissolution rates. Furthermore, most of these reactors or systems are configured for use with microorganisms in planktonic form, i.e., they exist as individual cells in liquid medium.

Existing bioreactors are either small scale, unsuitable for large scale manufacturing processes, or custom designed, increasing manufacturing and installation costs. Submerged membrane modules for wastewater treatment, such as the Puron™ MBR Module Model PSH-1500 from Koch Membrane Systems (Wilmington, Mass.), have been used in water and wastewater treatment for filtration and biological wastewater treatment. Wastewater and sludge is maintained outside a fiber of microporous hydrophilic membrane, and water is drawn into the center of the fiber through the microporous hydrophilic membrane to become treated water. Water fills both the shell side and center of the hollow fibers.

To get high yields and production rates the cell concentrations in the bioreactor need to be high and this requires some form of cell recycle or retention. Conventionally, this is achieved by filtration of the fermentation broth through microporous or nonporous membranes, returning the cells and purging the excess. These systems are expensive and require extensive maintenance and cleaning of the membranes to maintain the fluxes and other performance parameters.

Cell retention by formation of biofilms is a very good and often inexpensive way to increase the density of microorganisms in bioreactors. This requires a solid matrix with large surface area for the microorganisms to colonize and form a biofilm that contains the metabolizing microorganisms in a matrix of biopolymers that the microorganisms generate. Trickle bed and some fluidized bed bioreactors make use of biofilms to retain microorganisms on solid surfaces while providing dissolved gases in the liquid by flow past the solid matrix. They suffer from either being very large or unable to provide sufficient gas dissolution rates.

Particular forms of membranes have found use in supporting specific types of microorganisms for waste water treatment processes. U.S. Pat. No. 4,181,604 discloses the use of hollow fiber membranes for waste treatment where the outer surface of the fibers supports a layer of microorganisms for aerobic digestion of sludge.

U.S. patent application Ser. No. 11/781,717, filed Jul. 23, 2007; U.S. patent application Ser. No. 11/833,864, filed Aug. 3, 2007; and U.S. patent application Ser. No. 11/972,454, filed Jan. 10, 2008, disclose a membrane based bioreactor wherein anaerobic bacteria that have the ability to convert syngas to ethanol or other liquids have formed biofilms on the outer surface of hydrophobic membranes with the syngas fed to the bacterial biofilm through the inner surface of the membrane. Such a bioreactor system has been able to directly convert the primary components of synthesis gas, CO, and $H_2/CO_2$ to ethanol and other liquid products such as n-butanol, acetic acid, and butyric acid. In these systems the gas flows through a porous region of a hydrophobic membrane and then reaches a biofilm which is hydrophilic. One drawback of this arrangement is that if water reaches and deposits/condenses on the hydrophobic porous region it will severely decrease the gas transfer rate. When the biofilm grows on the outside of a hollow fiber membrane, this type of membrane system also lacks a direct means to promote the formation of a biofilm with an adequate thickness and control its performance.

Asymmetric membranes are known for use in a variety of membrane separations processes such as ultra and nano filtration. Asymmetric membranes are typically hydrophilic and have a relatively tight semi permeable "skin" layer on one side supported on a porous polymer layer. U.S. Pat. Nos. 4,442,206 and 4,440,853 show the use of the polymer layer in an asymmetric membrane to immobilize microorganisms for certain biological processes that use soluble carbon sources. However, the adaptation and use of such membranes for the anaerobic bioconversion of syngas to liquids has not been shown in the past.

Existing bioreactors are either small scale, unsuitable for large scale manufacturing processes, or custom designed, increasing manufacturing and installation costs. The costs of membrane housings and piping can be a significant addition to the cost of the membrane itself. Bioreactors have been unable to take advantage of standardized configurations and hardware that would improve the plant economics.

It would be desirable to have a horizontal array bioreactor for conversion of syngas components to liquid products that would overcome the above disadvantages.

SUMMARY OF THE INVENTION

It has been found that contacting syngas components such as CO or a mixture of $CO_2$ and $H_2$ with a surface of a membrane that contains a biolayer of microorganisms and permeating liquid to and from the opposite side of the membrane will provide a stable system for producing liquid products such as ethanol, butanol, hexanol, and other chemicals. The membrane has an asymmetric construction that provides a porous side, referred to herein as a biolayer, that provides pores to promote and control the growth of microorganism colonies therein while also exposing a surface over which to directly feed the microorganisms with syngas. Simultaneously another layer of the asymmetric membrane having less permeability than the biolayer, herein referred to as a hydration layer, permeates liquid from the opposite side of the asymmetric membrane. Accordingly, this invention is a membrane supported bioreactor system for conversion of syngas components such as CO, $CO_2$, and $H_2$ to liquid fuels and chemicals by anaerobic microorganisms supported on or within the surface of membrane and in direct contact with the gas phase syngas components. The liquid products produced in the biolayer on the membrane's gas contact side pass through the membrane and into a liquid stream that recovers the desired liquid products while also supplying nutrients to the biolayer in the reverse direction of liquid product flow.

One embodiment of this invention includes a membrane bioreactor for anaerobic conversion of gas into liquid products including a plurality of membrane modules having a plurality of hollow fibers, each of the plurality of hollow fibers having an asymmetric membrane wall defining a porous biolayer about an outer surface of the membrane wall and a less permeable hydration layer around the hollow fiber lumen; a membrane vessel having an interior sealed from the ambient atmosphere for retaining the membrane modules surrounded by a process gas in communication about the outer surface of the hollow fiber wall for formation of a biolayer by interaction of microorganisms with the process gas and for the production of a liquid product, wherein the membrane vessel retains the membrane modules in a common horizontal plane across which the hollow fibers extend vertically; a liquid supply conduit for communicating a process liquid with the hollow fiber lumens of the hollow fibers for permeation of water and nutrients to the biolayer and permeation of liquid products from the biolayer into admixture with the process liquid; a liquid recovery conduit in communication with the hollow fiber lumens to recover the process liquid containing the liquid products from the membrane vessel; and, a gas supply conduit for supplying the process gas to the interior of the membrane vessel.

Another embodiment of this invention includes a bioreaction method including retaining a process gas in a membrane vessel under anaerobic conditions; maintaining a plurality of membrane modules in a horizontally spaced arrangement and at least partially surrounded in the process gas, the membrane modules having a plurality of hollow fibers, each of the plurality of hollow fibers having an asymmetric membrane wall defining a porous biolayer about the outer surface of the membrane wall and a less permeable hydration layer around the hollow fiber lumen; growing a biolayer of microorganisms within biopores along the outer surface of the hollow fibers and producing a liquid product by interaction of the microorganisms with the process gas; and, passing a process liquid into the hollow fiber lumens and exchanging the process liquid through the hollow fiber wall to supply water and nutrients to biolayer and withdraw the liquid product in admixture with the process liquid.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE INVENTION

Figure 1:
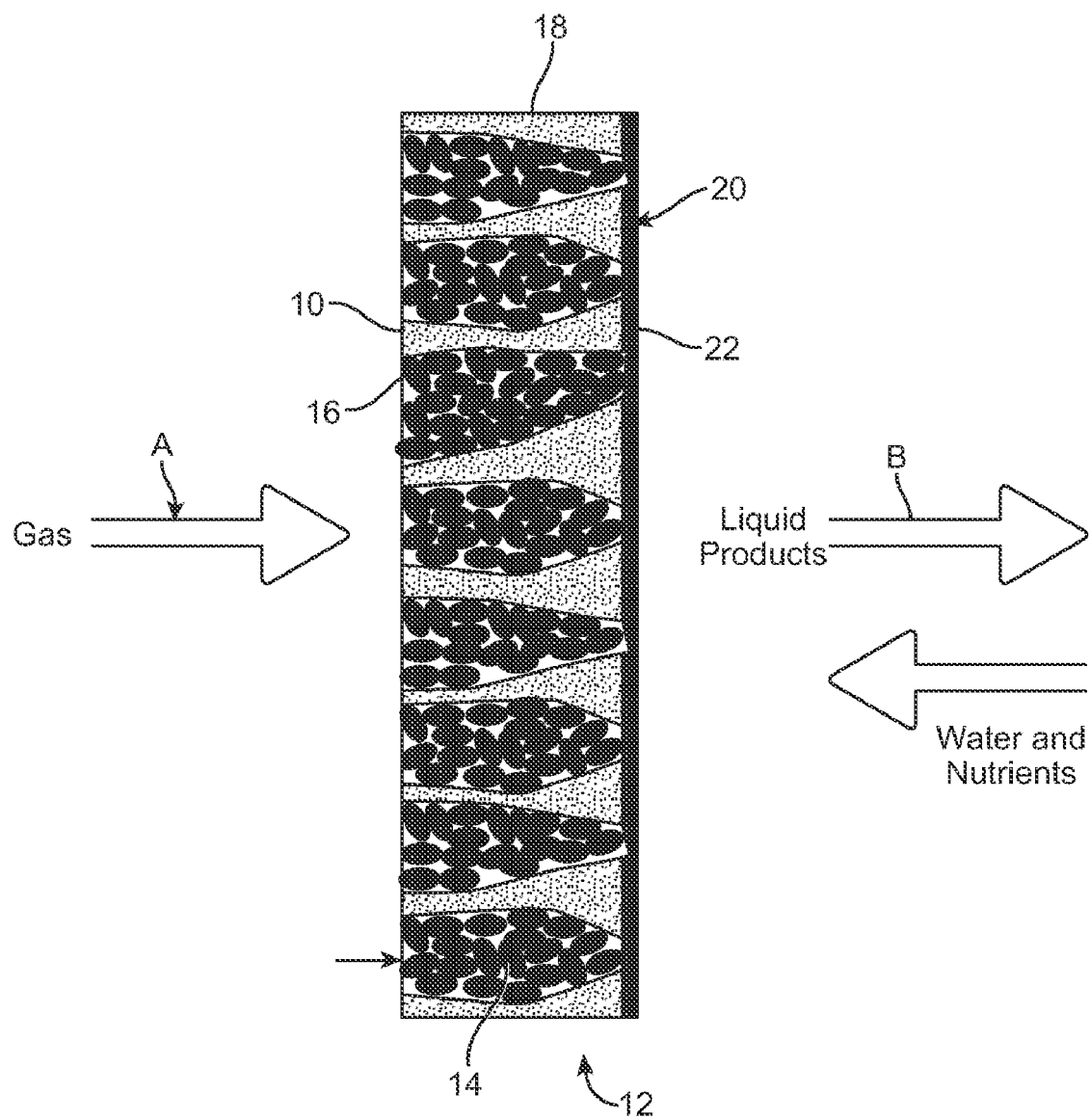
FIG. 1 is a schematic drawing of a cross-section of an asymmetric membrane with gas stream in contact with a biolayer that retains microorganisms therein and a hydration layer in the form of a skin in contact with liquid.

This invention is further described in the context of a bioconversion process for the production of ethanol from CO and/or mixtures of $H_2/CO_2$ using modules containing hollow fiber membranes. The description of the invention in a particular context does not restrict its application or claim coverage from other process applications that meet the criteria for its use.

This invention finds ready application to the production of acetic acid, ethanol, and other products from a feed gas stream. Such conversions using microorganisms are well known. For example, in a recent book concise description of biochemical pathways and energetics of such bioconversions have been summarized in "Electron Transport System in Acetogens," by A. Das and L. G. Ljungdahl, and "Diverse Physiologic Potential of Acetogens," by H. L. Drake and K. Kusel, appearing respectively as Chapters 14 and 13 of *Biochemistry and Physiology of Anaerobic Bacteria*, L. G. Ljungdahl, Ed., Springer (2003). Any suitable microorganisms that have the ability to convert the syngas components of CO, $H_2$, $CO_2$, individually or in combination with each other, or with other components that are typically present in syngas, may be utilized. Suitable microorganisms and/or growth conditions may include those disclosed in U.S. patent application Ser. No. 11/441,392, filed May 25, 2006, entitled "Indirect Or Direct Fermentation of Biomass to Fuel Alcohol," which discloses a biologically pure culture of the microorganism *Clostridium carboxidivorans* having all of the identifying characteristics of ATCC no. BAA-624; and U.S. patent application Ser. No. 11/514,385, filed Aug. 31, 2006, entitled "Isolation and Characterization of Novel Clostridial Species," which discloses a biologically pure culture of the microorganism *Clostridium ragsdalei* having all of the identifying characteristics of ATCC No. BAA-622; both of which are incorporated herein by reference in their entirety. *Clostridium carboxidivorans* may be used, for example, to ferment syngas to ethanol and/or n-butanol. *Clostridium ragsdalei* may be used, for example, to ferment syngas to ethanol.

Suitable microorganisms include the anaerobic bacteria *Butyribacterium methylotrophicum*, having the identifying characteristics of ATCC 33266 which can be adapted to CO and used. This enables the production of n-butanol as well as butyric acid as taught in the references: "Evidence for Production of n-Butanol from Carbon Monoxide by *Butyribacterium methylotrophicum*," in *Journal of Fermentation and Bioengineering*, vol. 72, 1991, pp. 58-60; and "Production Of Butanol And Ethanol from Synthesis Gas via Fermentation," in *FUEL*, vol. 70, May 1991, pp. 615-619. Other suitable microorganisms include *Clostridium ljungdahli*, with strains having the identifying characteristics of ATCC 49587 as disclosed in U.S. Pat. No. 5,173,429 entitled "Biological Production of Ethanol from Waste Gases with *Clostridium ljungdahlii*," and ATCC 55988 and 55989 as disclosed in U.S. Pat. No. 6,136,577 entitled "Biological Production of Ethanol from Waste Gases with *Clostridium ljungdahlii*." This will enable the production of ethanol as well as acetic acid. All of the above references are incorporated by reference herein in their entirety.

The microorganisms found suitable thus far for bioconversion for this invention require anaerobic growth conditions. Therefore, the bioconversion system employs suitable control and sealing methods to limit the introduction of oxygen into the system. Since the microorganisms contact the liquid that circulates through the bioreactor system, a suitable redox potential is maintained and monitored to insure anaerobic conditions. Anaerobic conditions in the liquid volume are usually defined as having a redox potential of less than −200 mV and preferably a redox potential in the range of from −300 to −500 mV. To further minimize exposure of the microorganisms to oxygen, the feed gas will preferably have an oxygen concentration of less than 1000 ppm, more preferably less than 100 ppm, and even more preferably less than 10 ppm.

The invention uses asymmetric membranes having a porous layer and a less permeable layer. The porous layer, referred to as the biolayer, can be any material suitable for the formation of the biopores and the transport of liquid to and away from the microorganisms in the biopores. The less porous layer, referred to as the hydration layer, controls the transport of the fermentation liquid to and from the biolayer for nourishing the microorganisms and maintains effluent products at desired concentrations. The biolayer and hydration layer are described as single layers, but either or both can include several layers.

The asymmetric membrane also requires material that provides support to the membrane structure and occludes the internal end of the biopores to prevent microorganisms and other biological material from passing into the fermentation liquid. The asymmetric membrane can contain additional layers for internal support and formation of the biopores or the biolayer and/or hydration layer may serve these functions as well. Any additional layers can permit direct contact of syngas with the microorganisms in the biopores and the permeation of liquid into the biolayer.

The biolayer defines the biopores for retaining the microorganisms in direct contact with the syngas. The biopores require an effective diameter of at least 1 µm over at least a portion of its length. The term effective diameter refers to the open cross-sectional area of a regularly shaped pore that would provide the same cross-sectional area. The pores need not have a uniform cross-section and biopores having an effective diameter of 1 µm over at least a third of its length are suitable. The biopores in the biolayer of the membrane usually have an effective diameter substantially greater than 1 µm, preferably in the range of 2 to 100 µm, and most preferably in the range of 5 to 50 µm. Typical depths of the biopores range from 50 to 500 µm which generally corresponds to the thickness of the biolayer.

The hydration layer can have restricted liquid permeability with respect to the biolayer. The restricted permeability prevents excessive fermentation liquid from migrating into the biolayer during normal operation of the system and interfering with contact between the gas and microorganisms. In most cases, the hydration layer is a higher density material than the biolayer that restricts liquid flow while also occluding the internal end of the biopores to block migration of the microorganisms into the fermentation liquid.

Particularly suitable forms of asymmetric membranes are porous membranes with a tight (i.e., having small pores) thin "skin" on one surface of the membrane that provides the hydration layer and a relatively open support structure underneath the skin that provides the biolayer and defines the biopores. The skin will typically comprise a semi-permeable layer having a thickness of from 0.5 to 10 µm. The skinned asymmetric membrane can include an "integrally skinned" membrane prepared by using phase inversion of one polymer or a composite membrane, where a thin layer of a certain material is formed on top of a porous sublayer of a same or different material. General description of asymmetric membranes and methods of their preparation can be found in the literature (e.g., M. Cheryn, *Ultrafiltration and Microfiltration Handbook*, Technomics Publishing Company, Lancaster, Pa., 1998; and M. Mulder, *Basic Principles of Membrane Technology*, 2$^{nd}$ *Edition*, Kluwer Academic Publishers, Norwell, Mass., 1996).

A suitable skin layer has a pore size that is smaller than the size of microbial cells to prevent the cells from passing through the membrane skin but the opposite surface of the membrane has large openings that allow cells to enter and leave the biopores of the membrane wall. Typically, the pore size of the skin layer is less than 0.5 µm, preferably less than 0.25 µm, and most preferably in the ultrafiltration range of nominal MWCO of 10 to 300 kDa and more preferably in the range of 10 to 100 kDa.

Several asymmetric ultrafiltration membranes are available from Millipore Corporation (Bedford, Mass.), including but not limited to the Amicon Membranes and the Ultracel PLC Membranes. The Amicon Membranes are made of polyethersulfone and with a range of a nominal MWCO, for example a nominal MWCO of 30 kDa for Amicon PM30. The Ultracel PLC Membranes, which are composite membranes made from casting the regenerated cellulose membrane onto a microporous polyethylene substrate, are available in the pore size range from 5 kDa (PLCCC) to 1000 kDa (PLCXK).

Additional examples of asymmetric membranes are the MMM-Asymmetric Super-Micron Membranes and BTS Highly Asymmetric Membranes, both available from Pall Corporation (East Hills, N.Y.). The MMM-Asymmetric Membranes, available in pore size range from 0.1 to 20.0 µm, are made of polysulfone and polyvinylpyrrolidone. The BTS Highly Asymmetric Membranes, available in pore size range from 0.05 to 0.80 µm, are cast of polysulfone with a "cut off" layer of about 10 µm and a total thickness of about 120 µm.

Hollow fiber membrane modules containing asymmetric ultrafiltration membranes are commercially available from a number of membrane manufacturers. For example, the Kros-Flo® Max Module Model KM5S-800-01N from Spectrum Laboratories (Rancho Dominguez, Calif.) has 22.0 m$^2$ membrane surface area of asymmetric polysufone hollow fiber membranes with 0.5 mm fiber inner diameter, a tight skin on the lumen side, and a pore rating of 50 kDa. ROMICON® polysulfone hollow fiber membranes available from Koch Membrane Systems (Wilmington, Mass.) are also asymmetric with the tight skin on the lumen side. ROMICON cartridge Model HF-97-43-PM50 is a 6-inch module containing fibers of 1.1 mm inner diameter and 50 kDa nominal MWC at 9.0 m$^2$ total membrane surface area.

Membranes of the various geometries and compositions described above may be used in arrangements of unitary arrays or assemblies of varied composition in the systems of this invention. Any suitable potting technique can be used to collect and provide the necessary assembly of individual membrane elements. In such membranes the gas and liquid can be brought into direct and intimate contact at the gas contact surface of the biolayer. Liquid is passed in the liquid side of the membranes via pumping, stirring, or similar means to remove the ethanol and other soluble products formed; the products are recovered via a variety of suitable methods.

The syngas flows through the gas chamber or channels of the bioreactor system continuously or intermittently. The feed gas pressure is in the range of 1 to 1000 psig, preferably 5 to 400 psig, and most preferably 10 to 200 psig. The differential pressure between the liquid and gas phases is managed in a manner that the membrane integrity is not compromised (e.g., the burst strength of the membrane is not exceeded) and the desired gas-liquid interface phase is maintained.

The gas side pressure is normally slightly higher than the liquid pressure to prevent convective liquid flow from the hydration layer (liquid) side to the open surface (gas) of the gas contacting side. The higher pressure also avoids formation of a liquid layer at the cell/gas interface, which would impede gas transfer to the cells.

When the feed syngas contains moisture, condensation of water can occur at the microorganism/gas interface as consumption of syngas results in supersaturation of water. This condensed water leaves the cell/gas interface by dripping to the bottom of the bioreactor due to gravity as well as by convective flow through the membrane due to the slightly higher pressure of the gas.

FIG. 1 is a schematic drawing showing a cross-section of an asymmetric membrane with a gas stream in contact with a biolayer that retains microorganisms therein and a hydration layer in the form of a skin in contact with liquid. An asymmetric membrane, suitable for permeation of the fermentation liquid, provides separation between the liquid phase and feed gas comprising at least one of CO or a mixture of $H_2$ and $CO_2$. FIG. 1 shows detail of the membrane configuration and interface in the operation of a representative bioreactor system. FIG. 1 depicts a cross-section of a single membrane element with a syngas stream A flowing to the gas contacting side 10 of the asymmetric membrane 12. The syngas components directly contact the microorganisms 14 contained in biopores 16. An anaerobic acetogenic bacteria, such as *Clostridium ragsdaeli* having all of the identifying characteristics of ATCC No. BAA-622, is maintained in the biopores 16 and is supplied with the fermentation liquid by permeation through the biolayer 18. The fermentation liquid circulates on the opposite side of the syngas stream A and permeates through a hydration layer formed as skin 20 on the inner surface of biolayer 18. Direct contact of the skin 20 with the biolayer 18 transfers the fermentation liquid to the biopores 16. The surfaces of biolayer 18 that contact the microorganisms and gas stream provide equilibrium partitioning across the asymmetric membrane to keep the liquid and gas phases separated from each other. The pores in the skin 20 are much smaller than the width of the microorganisms retained in the biopores 16 so that the skin 20 occludes the inner end of the biopores 16 and prevents the microorganisms from passing through the skin 20 and to liquid contacting surface 22. As a result, the microorganisms 14 preferentially stay within the biopores 16 to gain metabolic energy by converting CO and $H_2/CO_2$ thereby growing and sustaining themselves within the biopores 16. A portion of liquid B is withdrawn and separated to recover the desired products from the fermentation liquid.

To load the asymmetric membrane with microorganisms, the biolayer is first inoculated with microorganisms, followed by further cell growth to reach the desired cell loading density. To inoculate the biolayer, an aqueous solution containing microorganisms is introduced to the gas contacting side of the asymmetric membrane, and then the solution is slowly filtered through the biolayer and hydration layer by applying a slight trans-membrane pressure, creating a microorganism-free filtrate through the hydration layer and entrapping cells within the biopores of the biolayer. The microorganism-containing membrane is incubated for further microorganism growth, by contacting the membrane with a liquid solution containing nutrients and carbon source suitable for microorganism growth. Alternatively, the membrane can be incubated using a syngas and a liquid solution containing nutrients.

FIGS. 2 & 3 show various configurations of asymmetric membranes with microorganisms present within biopores of the biolayers.

FIG. 2, in which like elements share like reference numbers with FIG. 1, is a schematic drawing showing a central passage formed by two membranes of the type shown in FIG. 1 with a gas stream contacting the outer wall and liquid contacting the inner walls. Two asymmetric membranes 12 border a central liquid channel 24 through which a fermentation liquid circulates in the direction of stream C. The asymmetric membranes 12 on each side of liquid channel 24 function in a similar manner to that described for the single membrane element of FIG. 1. Syngas flows across gas contacting side 10 into contact with the microorganisms 14 and fermentation products pass out the skin 20 in the direction of arrows 26. The arrangement of FIG. 2 can use a flat sheet configuration or a tubular configuration and be particularly useful for good flow control and distribution on the liquid side.

FIG. 3 is a schematic drawing showing a transverse cross-section of the asymmetric membrane of FIG. 1 made into a hollow fiber with the biolayer on the outside and the hydration layer on the inside. FIG. 3 shows a special case of FIG. 2 wherein the asymmetric membrane 12' wraps around in continuous form to provide a tubular membrane with a central liquid channel 24'. In this case the syngas stream A flows radially inward into contact with the microorganisms 14 contained within an annular biolayer 18'. The skin 20' covers the inner surface of the biolayer 18' and controls the permeation of liquid across biolayer 18'.

In most operations the membrane arrangements will benefit from occasional purging or flushing of the biopores and gas contacting surfaces. For this purpose, periodically during syngas fermentation, the liquid pressure can be increased for a short time to become slightly higher than the gas pressure to create a liquid flow through the membrane to purge some accumulated dead microorganisms or biopolymers from the biopores and from the gas contacting surface. This water is collected from the gas stream side of the bioreactor. Optionally this water stream may be treated for removal of suspended solids and recirculated to the bioreactor system.

It can also be desirable to clean the biopores and biolayer. This process begins with substantially removing the immobilized cells and the cleaning the asymmetric membrane. The gas supply is stopped, and the membrane is cleaned with cleaning solutions in manners similar to typical cleaning of microfiltration and ultrafiltration membranes. For example, the asymmetric membrane can be first soaked in a cleaning solution from both the sides, e.g., the biolayer and hydration layer. The cleaning solution is formulated or selected to facilitate solubilization of microorganism and biopolymers. One of such solutions is an aqueous solution containing 2% NaCl and 0.4% NaOH, but many other formulations have been used for membrane cleaning, including some containing surfactants and hydrolytic enzymes. After soaking, the cleaning solution is circulated and a positive trans-membrane pressure is applied from the hydration layer side to create a convective flow through the membrane and flush microorganism and biopolymers out through the gas contacting surface of the biolayer. The soaking-filtration procedures can be repeated as needed, and different cleaning solutions can be used. After membrane cleaning, the membrane can be used for loading and growing new cells for syngas fermentation again.

Finally, the asymmetric membrane may benefit from a periodic surge of liquid from channel 24 toward the biopores followed by backflush of the liquid from the biopores to channel 24. This periodic laving of the liquid enhances the delivery of nutrients to the microorganisms and the recovery of liquid products from the biopores. The laving cycle differs significantly from the previously described purging since the laving cycle will occur more often than purging and seeks to avoid any discharge of liquid from the biopores.

Therefore laving, like purging occurs by temporarily increasing the relative liquid pressure to gas pressure across the membrane but to a lesser degree than effected during the purge cycle. Co-pending U.S. patent application Ser. No. 12/258,193, filed Oct. 24, 2008, contains additional information related to laving and is incorporated herein by reference in its entirety.

FIG. 4 is a schematic drawing of a two-headed membrane module for use in a bioreactor system with gas and liquid circulation. Each membrane module provides a large surface area of asymmetric hydrophilic membranes in the form of hollow fibers. The hollow fibers are oriented vertically. A number of the membrane modules can be located in a closed membrane vessel containing process gas, so that a very large total membrane surface area can be achieved with a small number of membrane vessels, simplifying plant design and reducing costs. The membrane vessel can be round, square, rectangular or any other suitable shape with gas-tight cover plates on the top. In the arrangement and method of this invention process liquid fills the hollow fiber lumens, while a biolayer and process gas are on the shell side of hollow fibers. Those skilled in the art will appreciate that the membrane modules can have any cross section as desired for a particular purpose, such as round, rectangular, square, or any other cross section that accommodates a desired pitch and/or spacing.

Each of the membrane modules has a number of hollow fibers and each of the hollow fibers has an asymmetric hollow fiber wall defining a hollow fiber lumen and an outer surface. A process liquid is disposed in the hollow fiber lumens and a biolayer is disposed on or within the outer surface of the hollow fibers. Process gas passes through the hollow fiber wall to interact with the biolayer and generate a liquid product that mixes with the process liquid. Process liquid passes through the hollow fiber wall in the opposite direction to provide water and nutrients to the biolayer. The process gas can be a synthesis gas (syngas), such as a mix of CO, $H_2$, and $CO_2$ with other components such as $CH_4$, $N_2$, $NH_3$, $H_2S$, and other trace gases, or the like. The biolayer supports a culture, such as *Clostridium ragsdalei, Butyribacterium methylotrophicum, Clostridium ljungdahlii, Clostridium carboxidivorans*, combinations thereof, and the like, which can generate the liquid product from the syngas. The liquid product can be ethanol, n-butanol, hexanol, acetic acid, butyric acid, combinations thereof, and the like, depending on the syngas and culture selected. Those skilled in the art will appreciate that numerous combinations of syngas and culture can be selected as desired for generating a particular liquid product desired.

Figure 2:
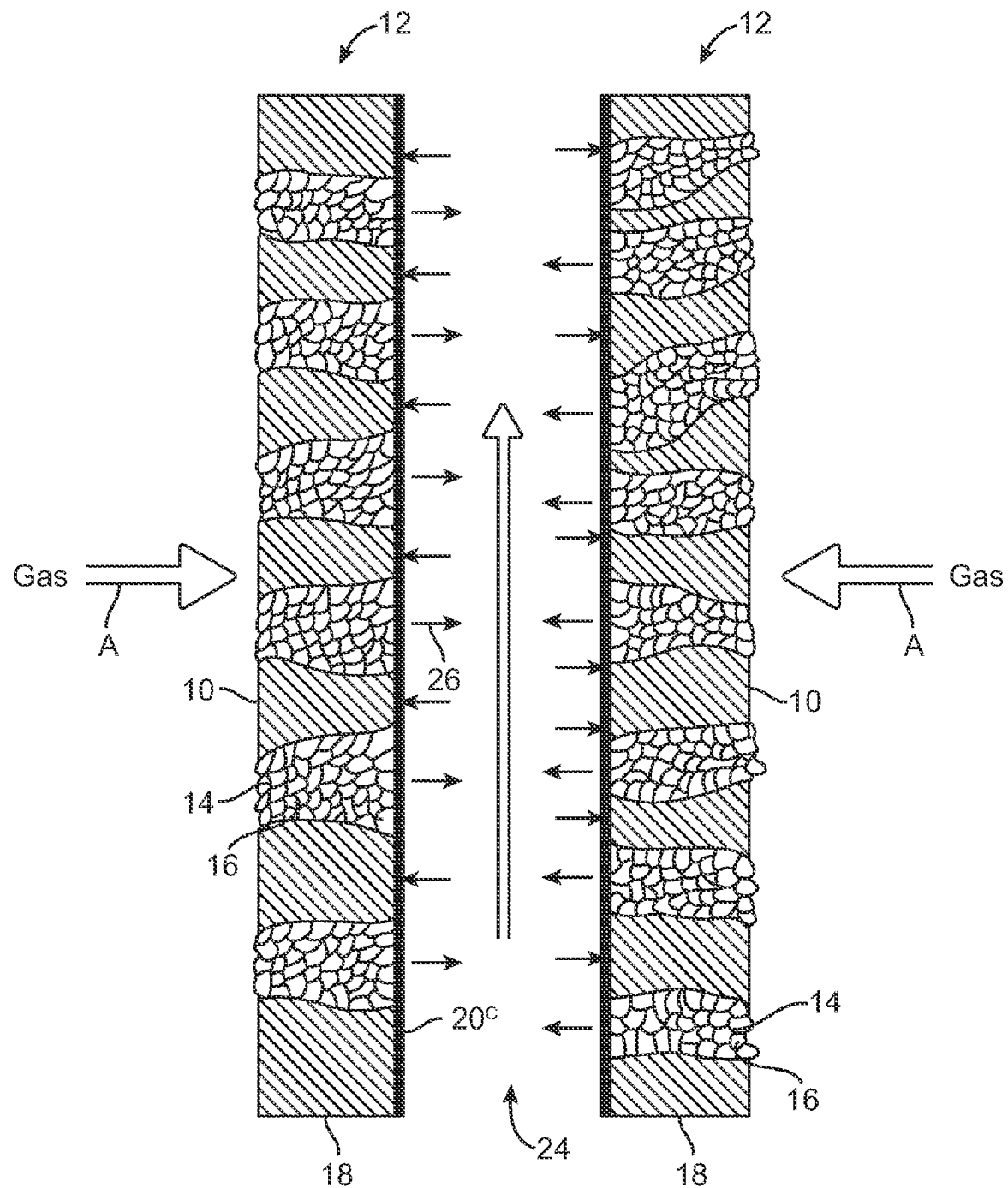
FIG. 2 is a schematic drawing of a central passage formed by two membranes of the type shown in FIG. 1 with a gas stream contacting the outer wall and liquid contacting the inner walls.
Figure 3:
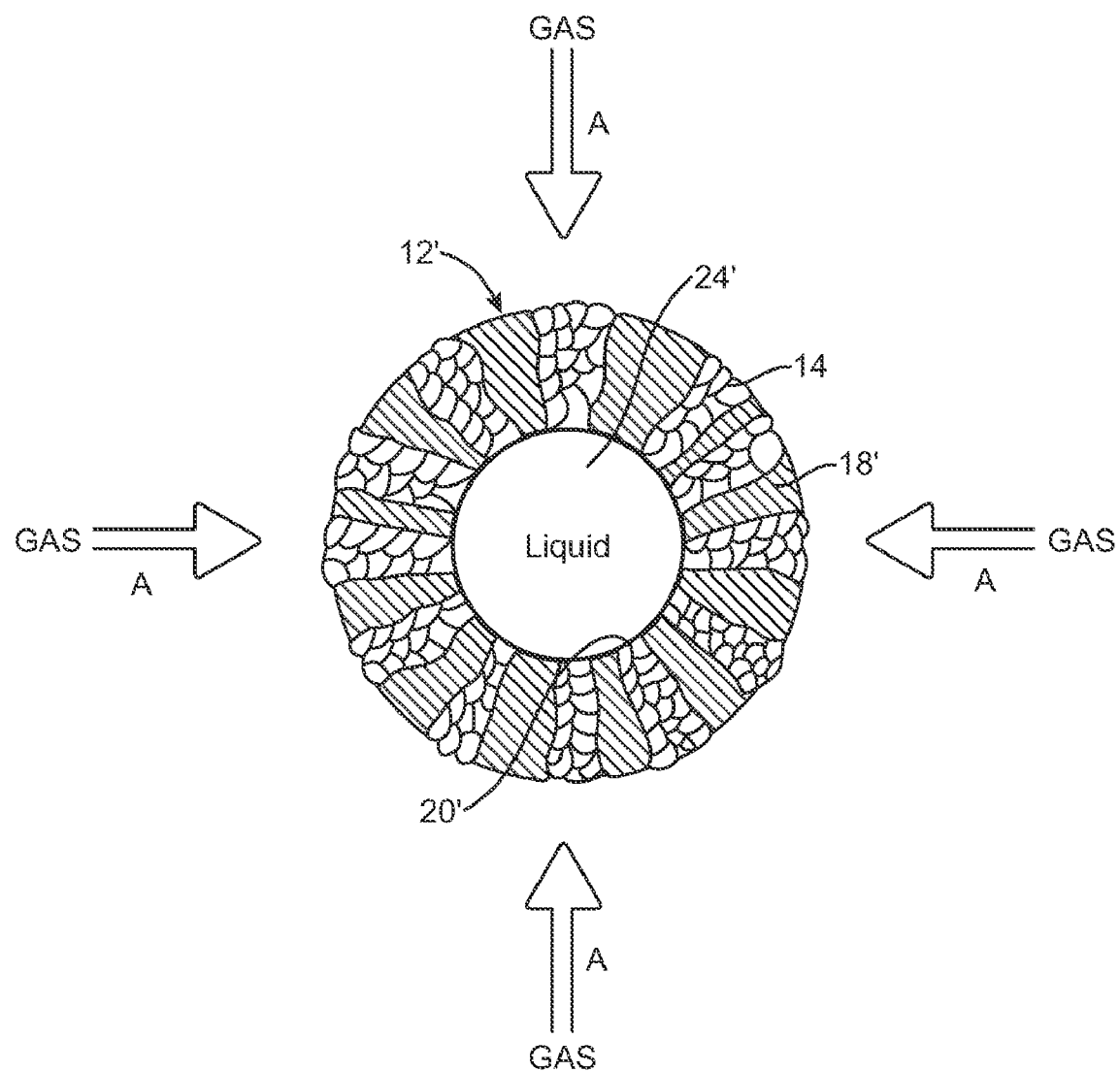
FIG. 3 is a schematic drawing of a transverse cross-section of the asymmetric membrane of FIG. 1 made into a hollow fiber with the biolayer on the outside and the hydration layer on the inside.
Figure 4:
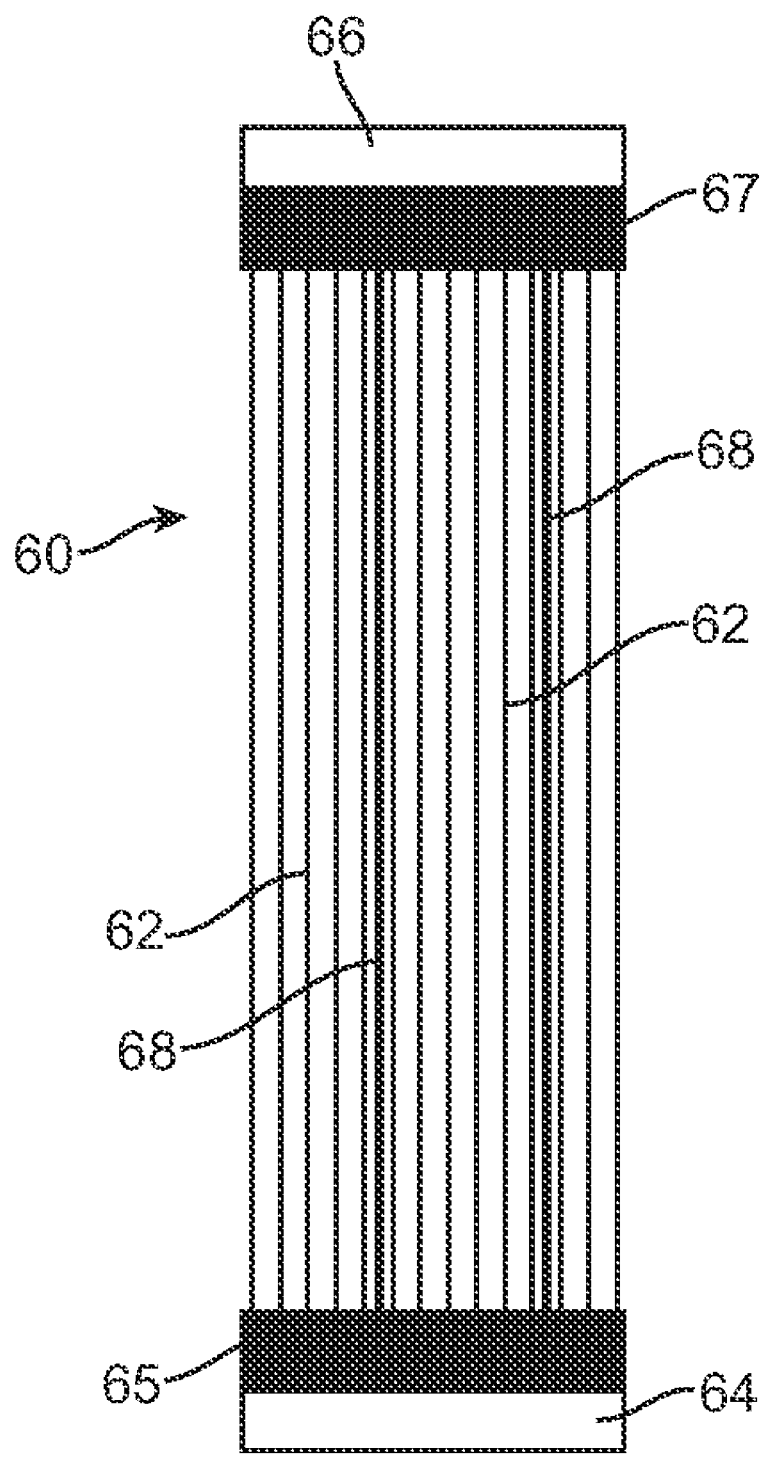
FIG. 4 is a schematic drawing of a two-headed membrane module for use in a bioreactor system with gas and liquid circulation.

FIG. 4 illustrates a two-headed membrane module. The membrane module 60 can include hollow fibers 62 as shown in FIGS. 2 & 3. The hollow fibers 62 define biopores that open to the outer surface of the hollow fibers and contain the biolayer. In this arrangement, the membrane module 60 includes a number of hollow fibers 62, each having a hollow fiber wall defining a hollow fiber lumen and an outer surface. A liquid inlet chamber 64 is operably connected to one end of the hollow fibers 62 through potted end 65 to provide the process liquid to the hollow fiber lumens and a liquid outlet chamber 66 is operably connected to the other end of the hollow fibers 62 through potted end 67 to receive the process liquid from the hollow fiber lumens. The potted end 65 is spaced apart from the potted end 67. The potted end 65 can be operably connected to a liquid supply conduit and the potted end 67 operably connected to a liquid recovery conduit, or vice versa, so the process liquid can flow through the hollow fiber lumens from one potted end to the other.

The hollow fibers 62 can be potted to the liquid inlet chamber 64 and the liquid outlet chamber 66 with an epoxy or the like. A number of support rods 68 connect the liquid inlet chamber 64 and the liquid outlet chamber 66 to provide mechanical strength to the membrane module 60, which must withstand forces caused by weight of the hollow fibers and biolayer, membrane module handling, and the like. The length of the hollow fibers 62 can be greater than the distance between the liquid inlet chamber 64 and the liquid outlet chamber 66 to give the hollow fibers 62 some slack and freedom to move. In one embodiment, the hollow fibers have a length equal to 1.015 to 1.15 times the distance between the first potted end 65 and the second potted end 67 to produce slack in the hollow fibers. In another embodiment, the hollow fibers have a length equal to 1.015 to 1.03 times the distance between the first potted end 65 and the second potted end 67 to produce slack in the hollow fibers.

Figure 5:
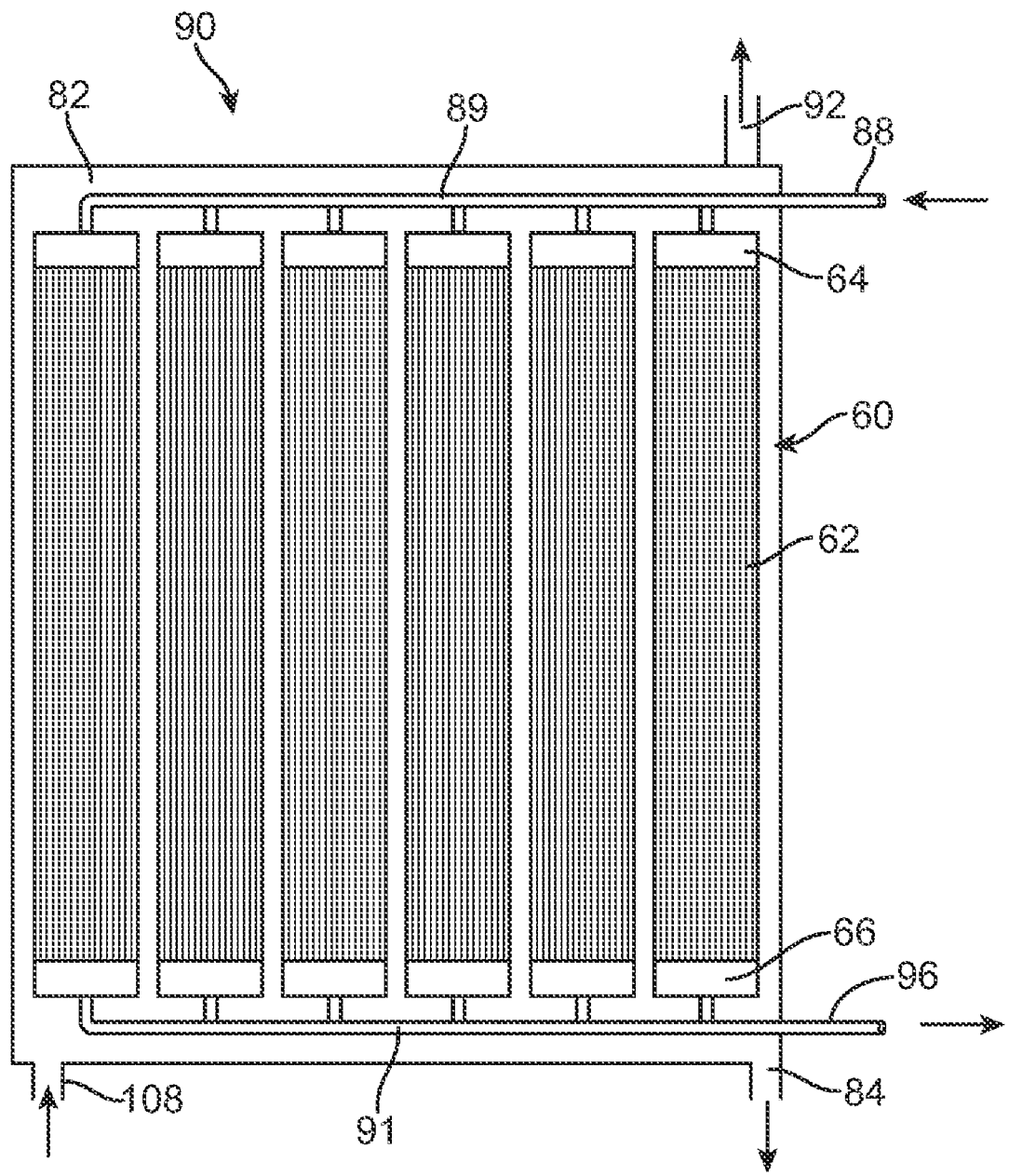
FIG. 5 is a schematic drawing of a bioreactor system with a plurality of two-headed membrane modules connected in parallel.

FIG. 5 is a schematic drawing of a bioreactor system with a plurality of two-headed membrane modules connected in parallel. In this embodiment, the membrane modules 60 are two-headed membrane modules as shown in FIG. 4 having a liquid inlet chamber 64 and a liquid outlet chamber 66. The liquid inlet chamber 64 and the liquid outlet chamber 66 are operably connected to the hollow fibers 62 to allow the process liquid to flow through the hollow fiber lumens from the liquid inlet chamber 64 to the liquid outlet chamber 66. The modular membrane bioreactor 90 includes a membrane vessel 80, process gas 82 disposed in the interior of the membrane vessel 80 and a number of membrane modules 60 connected in parallel and disposed in the process gas 82. The interior of the membrane vessel 80 is sealed from the ambient atmosphere to retain the membrane modules 60 surrounded by the process gas 82, which is in communication about the outer surface of the hollow fiber wall for formation of a biolayer by interaction of microorganisms with the process gas 82 and for the production of a liquid product. The membrane vessel 80 retains the membrane modules 60 in a common horizontal plane across which the hollow fibers 62 extend vertically.

A process liquid enters the membrane vessel 80 through liquid inlet 88 and is distributed to the liquid inlet chambers 64 of each of the membrane modules 60 through a liquid supply conduit 89. In this example, the process liquid flows downward through the membrane modules 60. The liquid supply conduit 89 communicates the process liquid with the hollow fiber lumens of the hollow fibers 62 for permeation of water and nutrients to the biolayer and permeation of liquid products from the biolayer into admixture with the process liquid. The process gas 82, such as syngas or the like, enters the membrane vessel 80 through gas inlet port 108 and exits the membrane vessel 80 through gas outlet port 92. In one example, the process gas 82 can be at least one of CO or a mixture of $CO_2$ and $H_2$. The gas inlet port 108 can be a gas supply conduit for supplying the process gas to the interior of the membrane vessel 80. As the process liquid flows along the length of the hollow fibers 62, the process liquid transfers through the membrane of the hollow fibers 62 and generates liquid product, such as ethanol or the like, through interaction with the biolayer on the outer surface of the hollow fibers 62. In one example, the biolayer can contain microorganisms such as *Clostridium ragsdalei, Butyribacterium methylotrophicum, Clostridium ljungdahlii, Clostridium carboxidivorans*, and combinations thereof. In one example, the liquid product can be ethanol, n-butanol, hexanol, acetic acid, butyric acid, and combinations thereof. The liquid product transfers back through the membrane of the hollow fibers 62 and mixes into the process liquid within the hollow fiber lumens.

The process liquid exits the hollow fibers 62 into the liquid outlet chambers 66, which are connected to a liquid outlet 96 through a liquid recovery conduit 91, which is in communication with the hollow fiber lumens to recover the process liquid containing the liquid products from the membrane vessel 80. The liquid product can then be separated from the process liquid with a product recovery system operably connected to receive the process liquid from the liquid recovery conduit 91, to separate the liquid product from the process liquid, and to return process liquid to the membrane vessel 80. In one embodiment, recycle liquid including fresh liquid and/or recycled broth, i.e., process liquid at least partially stripped of the liquid product, can be returned to the modular membrane bioreactor 90 at the liquid inlet 88. In one embodiment, the gas outlet port 92 can be closed to maximize process gas utilization efficiency. Those skilled in the art will appreciate that the membrane modules 60 can be grouped into two or more banks of membrane modules 60 within the membrane vessel 80 and with each bank of the membrane modules 60 having an independent flow of process fluid.

The membrane vessel 80 further includes a shell side drain 84 to drain liquid from the membrane vessel 80. Liquid can be present on the shell side during normal and transitional operation. During normal operation, condensation and/or leakage can cause liquid to accumulate within the membrane vessel 80. During startup, liquid including suspended microorganisms is filtered from the shell side of the membrane vessel 80 through the hollow fibers 62 to establish the microorganisms within the biopores and the liquid drained through the shell side drain 84. During purging or flushing of the biopores and gas contacting surfaces, pressure of the process liquid within the hollow fibers 62 is increased so the process liquid flows through the wall of the hollow fibers 62 into the membrane vessel 80 and the residue is drained through the shell side drain 84. During cleaning of the biopores and biolayer, cleaning solution can be circulated within the membrane vessel 80 and drained through the shell side drain 84.

Figure 6:
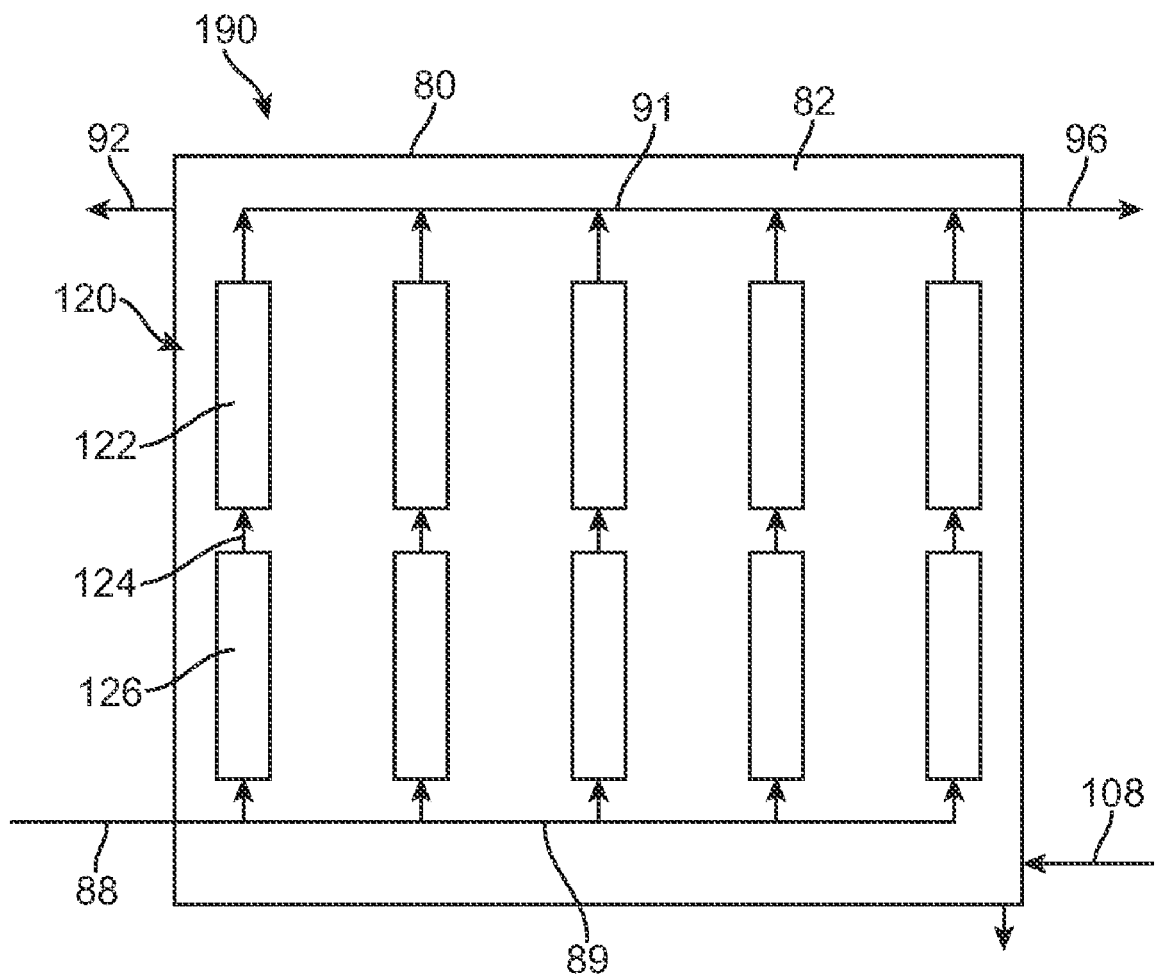
FIG. 6 is a schematic drawing of a bioreactor system with series stacked two-headed membrane modules connected in parallel.

FIG. 6, in which like elements share like reference numbers with FIG. 5, is a schematic drawing of a bioreactor system with series stacked two-headed membrane modules connected in parallel. In this embodiment, the membrane modules 120 are a plurality of membrane modules arranged in axial stacks contained in the bioreactor 190. A conduit 124 communicates process liquid from one membrane module 126 to an adjacent membrane module 122 in each stack of the membrane module 120. Each of the membrane modules 122, 126 has a liquid inlet chamber operably connected to the first potted end of the membrane module 122, 126 and a liquid outlet chamber operably connected to the second potted end of the membrane module 122, 126. The liquid outlet chamber of at least one membrane module 122, 126 communicates with the inlet chamber of an adjacent membrane module 122, 126.

Figure 7:
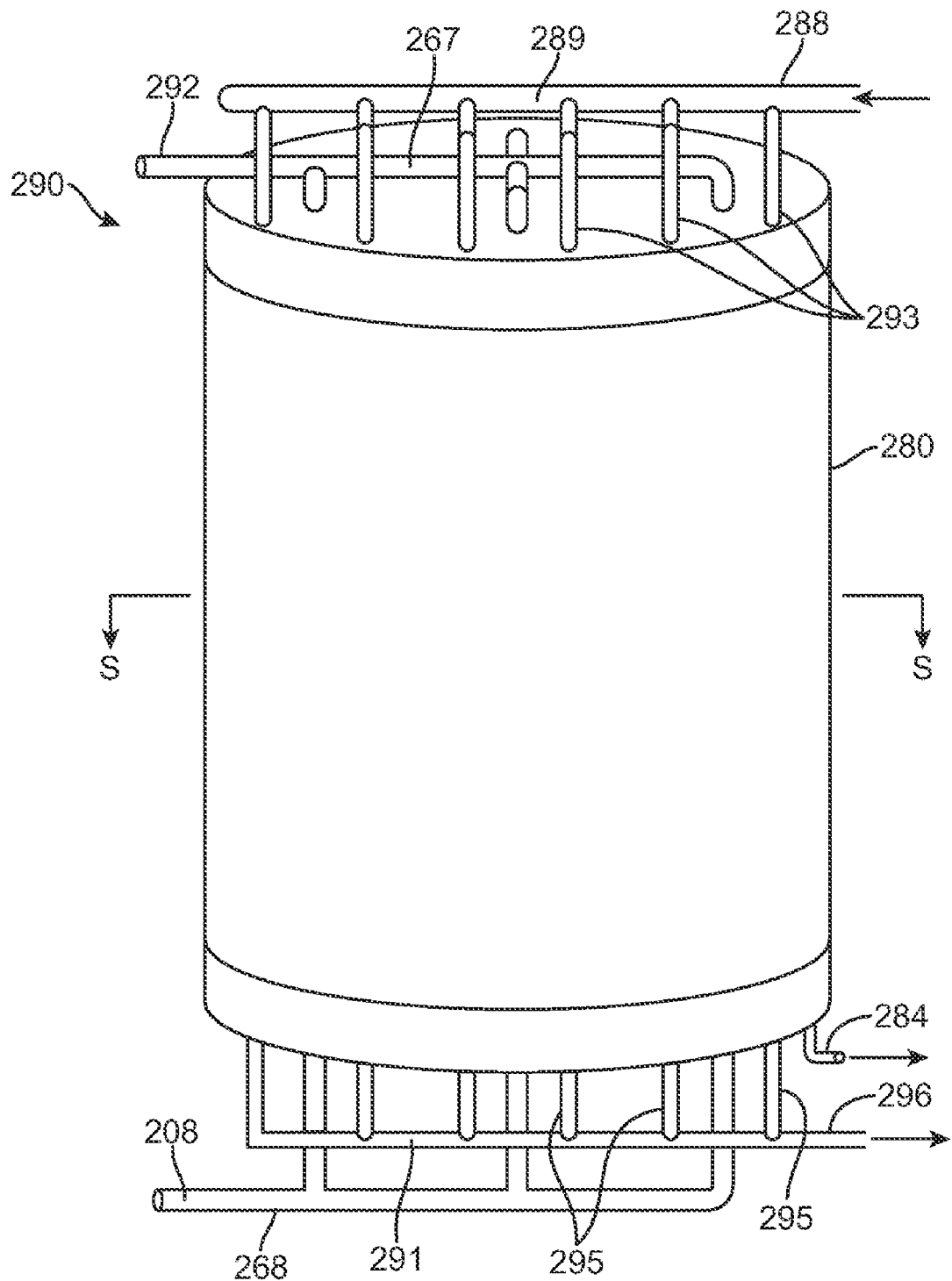
FIG. 7 is a schematic drawing of a membrane vessel for retaining a group of membrane modules as a single bank in a bioreactor system.
Figure 8:
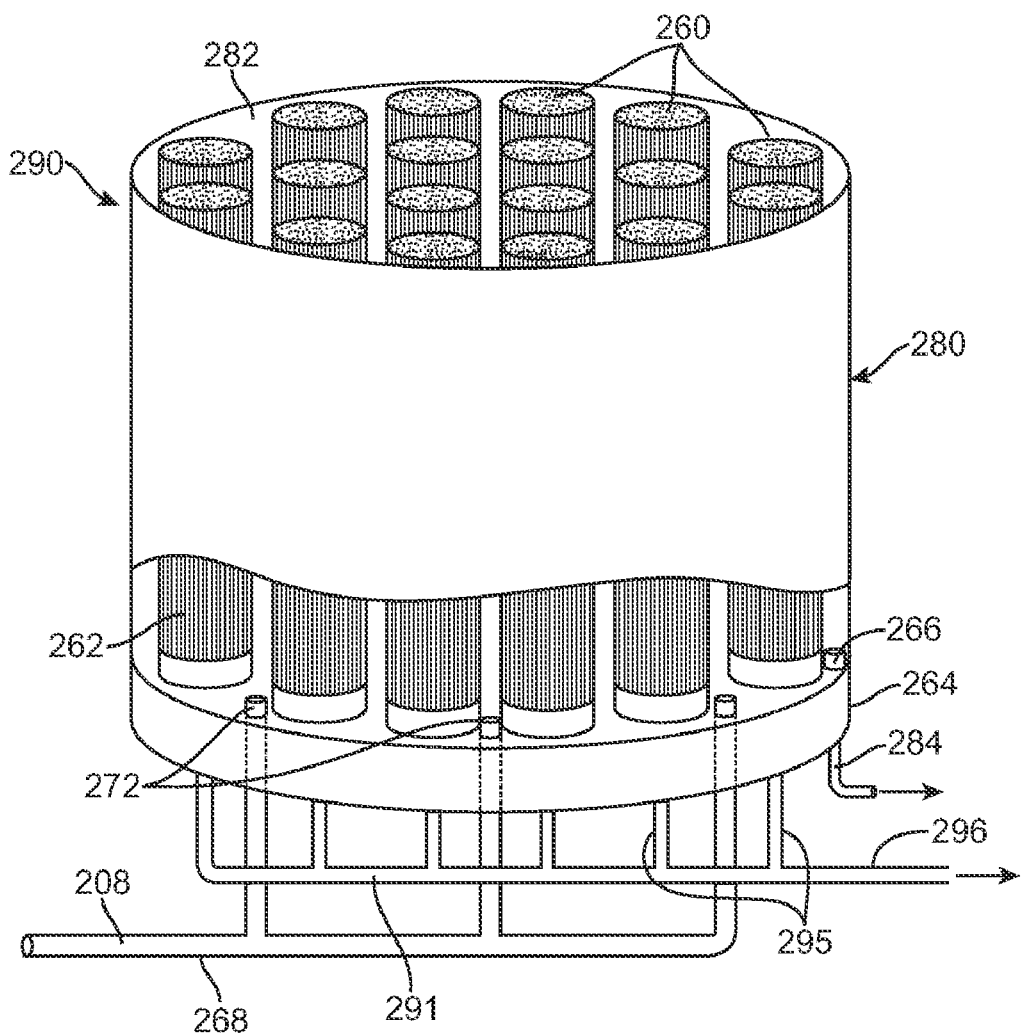
FIG. 8 is a section and cutaway view of the membrane modules in the bank of FIG. 7.

FIGS. 7 & 8 schematically depict an assemblage of multiple membrane modules as generally illustrated in FIG. 5. FIG. 7 is a schematic drawing of a membrane vessel for retaining a group of membrane modules as a single bank in a bioreactor system and FIG. 8 is a section and cutaway view of the membrane modules in the bank of FIG. 7.

In this embodiment, the membrane modules 260 are two-headed membrane modules as shown in FIG. 4 having a liquid inlet chamber and a liquid outlet chamber. The liquid inlet chamber and the liquid outlet chamber are operably connected to the hollow fibers 262 to allow the process liquid to flow through the hollow fiber lumens from the liquid inlet chamber to the liquid outlet chamber. The modular membrane bioreactor 290 includes a membrane vessel 280, process gas 282 disposed in the membrane vessel 280 and a number of membrane modules 260 connected in parallel and disposed in the process gas 282.

A process liquid enters the membrane vessel 280 through liquid inlet 288 and is distributed to the liquid inlet chambers of each of the membrane modules 260 through a liquid supply conduit 289 having branch lines 293. The process liquid is distributed from the liquid inlet chamber into the hollow fiber lumen of each hollow fiber 262. The process gas 282, such as syngas or the like, enters the membrane vessel 280 through gas inlet port 208 and lower piping network 268, and exits the membrane vessel 280 through upper piping network 267 and gas outlet port 292. In one embodiment, the gas pressure in the membrane vessel 280 is between 100 and 150 psi. In this example, the lower piping network 268 is the gas supply conduit, although the process gas flow can be reversed through the membrane vessel 280 so the upper piping network 267 becomes the gas supply conduit. As the process liquid flows along the length of the hollow fibers 262, the process liquid transfers through the membrane of the hollow fibers 262 and generates liquid product, such as ethanol or the like, through interaction with the biolayer on the outer surface of the hollow fibers 262. The liquid product transfers back through the membrane of the hollow fibers 262 and mixes into the process liquid within the hollow fiber lumens. The process liquid exits the hollow fibers 262 into the liquid outlet chambers, which are connected to a liquid outlet 296 through a liquid recovery conduit 291 having branch lines 295. The liquid product can then be separated from the process liquid. In one embodiment, recycle liquid including fresh liquid and/or recycled broth, i.e., process liquid at least partially stripped of the liquid product, can be returned to the modular membrane bioreactor 290 at the liquid inlet 288. In one embodiment, the gas outlet port 292 can be closed to maximize process gas utilization efficiency.

The membrane vessel 280 further includes a shell side drain 284 to drain liquid from the membrane vessel 280. Liquid can be present on the shell side during normal and transitional operation. During normal operation, condensation and/or leakage can cause liquid to accumulate within the membrane vessel 280. During startup, liquid including suspended microorganisms is filtered from the shell side of the membrane vessel 280 through the hollow fibers 262 to establish the microorganisms within the biopores and the liquid drained through the shell side drain 284. During purging or flushing of the biopores and gas contacting surfaces, pressure of the process liquid within the hollow fibers 262 is increased so the process liquid flows through the wall of the hollow fibers 262 into the membrane vessel 280 and the residue is drained through the shell side drain 284. During cleaning of the biopores and biolayer, cleaning solution can be circulated within the membrane vessel 280 and drained through the shell side drain 284.

FIG. 8 depicts additional details of the membrane module and piping arrangement within and about the membrane vessel 280 through a section taken along line S-S in FIG. 7 and partial cut-away view at the bottom of the membrane vessel 280. The membrane vessel 280 houses a plurality of individual membrane modules 260. Each membrane module 260 is of the type shown in FIG. 4 having open sidewalls for communication of process gas that enters or leaves the membrane vessel 280 through ports 272 that communicate the gas stream through bottom plate 264 and with lower piping network 268. Each port 272 can protrude slightly from the bottom plate 264 to keep liquid from entering the lower piping network 268 during the purge step. Drain port 266 collects liquid from inside the membrane vessel 280 for removal through the shell side drain 284.

When the membrane vessel 280 operates at high pressure, the membrane vessel 280 may incorporate a pressure balancing head (not shown) with appropriate geometry to more efficiently withstand the pressure load and reduce the required thickness of the bottom plate 264.

Figure 9:
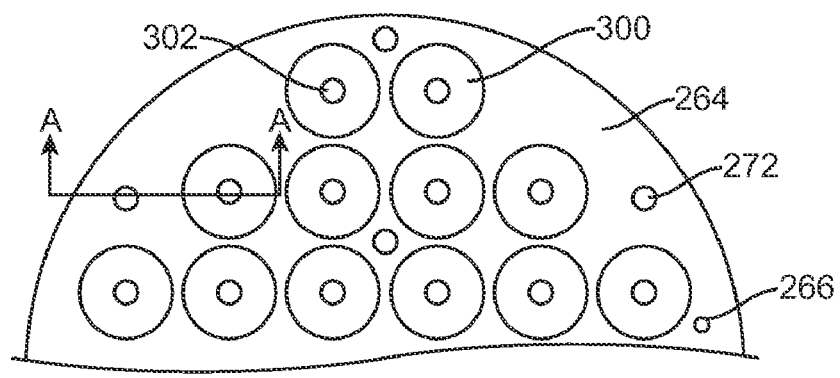
FIG. 9 is a top view of the bottom plate in the membrane vessel of FIG. 7.

FIG. 9 is a top view of the bottom plate in the membrane vessel of FIG. 7. In this embodiment, the bottom plate 264 defines recesses 300 to receive and support the lower portion of the membrane module. Each recess 300 includes an opening 302 permitting process liquid to communicate between the branch lines of the outlet header and the membrane module. The bottom plate 264 further defines the drain port 266, which collects liquid from inside the membrane vessel for removal through the shell side drain, and the ports 272, which communicate the gas stream through bottom plate 264 and with lower piping network. The bottom plate 264 can be contoured so liquid on the bottom plate 264 runs toward the drain port 266. Those skilled in the art will appreciate that the pitch and/or size of the recesses 300 can be set as desired for a particular application, depending on the desired pitch, packing, and shape of the membrane modules.

Figure 10:
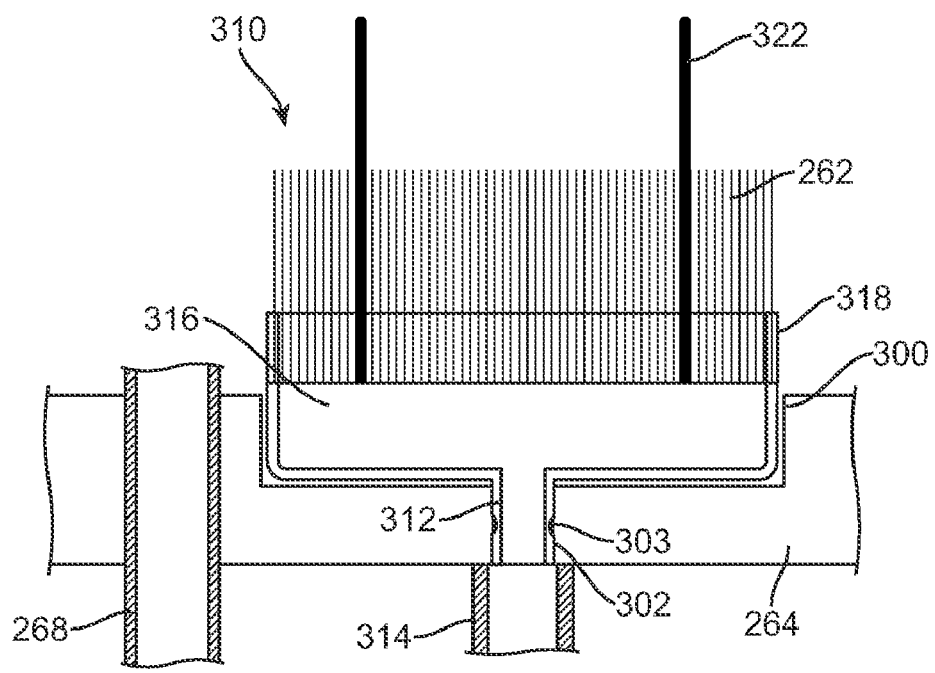
FIG. 10 is a detail cross-section view of a support arrangement for the membrane modules in the bank of FIG. 7.

FIG. 10 is a detail cross-section view of a support arrangement for the membrane modules in the bank of FIG. 7. The cross-section is across section A-A of FIG. 9. In this embodiment, the bottom plate 264 defines a recess 300 to receive and support the lower portion of the membrane module 310. The recess 300 includes an opening 302 that receives an extension 312 of the membrane module 310. Process liquid flows through the branch line 314, the extension 312, the liquid chamber 316, the potted end 318, and the hollow fiber lumens of the hollow fibers 262. A sealing element such as O-ring 303 prevents liquid from bypassing the extension 312 and entering the inter-module space. Support rods 322 connect the one potted end 318 of the membrane module 310 to the opposite potted end of the membrane module 310. Those skilled in the art will appreciate that suitable seals, such as an O-ring about the extension 312 or the like, can be provided between the membrane module 310 and the bottom plate 264 to separate the process liquid from the process gas. The bottom plate 264 further defines the drain port 266, which is lined with a pipe that protrudes slightly from the bottom plate 264 to keep liquid from entering the gas flow through the lower piping network 268.

Figure 11:
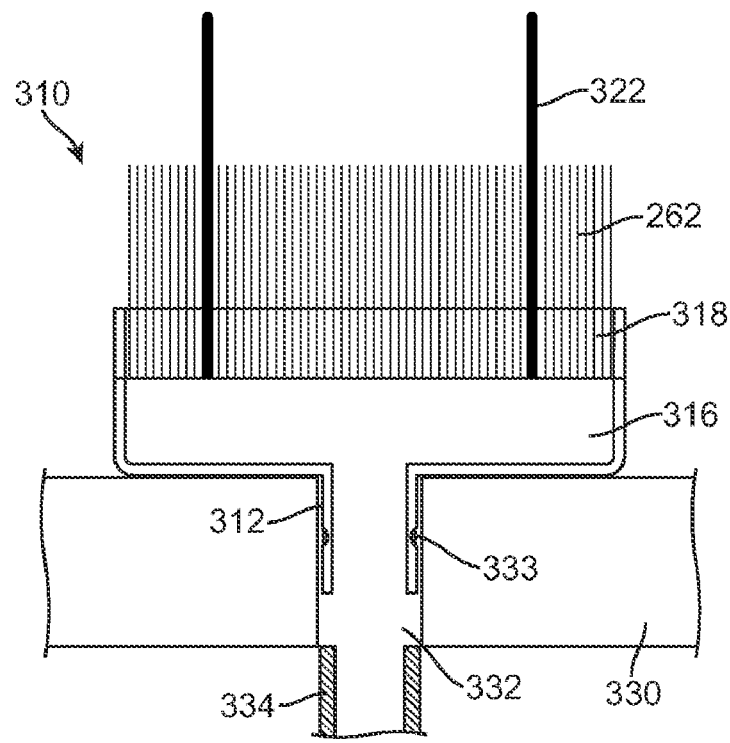
FIG. 11 is a detail cross-section view of another support arrangement for the membrane modules in the bank of FIG. 7.

FIG. 11 is a detail cross-section view of another support arrangement for the membrane modules in the bank of FIG. 7. In this embodiment, there is no recess in the bottom plate 330 to receive the membrane module 310, which rests on the bottom plate 330. The bottom plate 330 includes an opening 332 that receives an extension 312 of the membrane module 310. Process liquid flows through the branch line 334, the extension 312, the liquid chamber 316, the potted end 318, and the hollow fiber lumens of the hollow fibers 262. O-ring 333 seals the space outside extension 312 to prevent bypassing of liquid. Support rods 322 connect the one potted end 318 of the membrane module 310 to the opposite potted end of the membrane module 310. Those skilled in the art will appreciate that suitable seals, such as an O-ring about the extension 312 or the like, can be provided between the membrane module 310 and the bottom plate 330 to separate the process liquid from the process gas.

FIGS. 10 and 11 depict structures for a bottom support arrangement to receive the bottoms of the membrane modules. Similar structures may receive the tops of the membrane modules to secure them and connect nozzles for receiving liquid. In particular a removal top plate may provide the means to the seal the membrane vessel that retains the membrane modules while also supplying the means for retaining and connecting the upper ends of the membrane modules.

Figure 12:
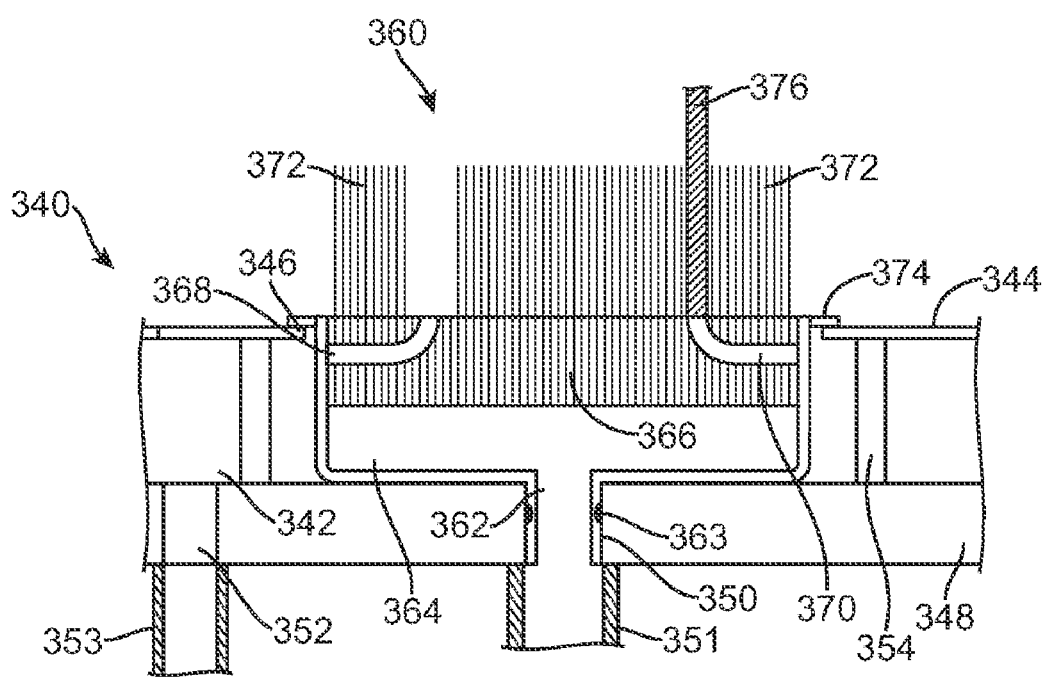
FIG. 12 is a detail cross-section view of a flow distribution arrangement for the membrane modules in the bank of FIG. 7.
Figure 13:
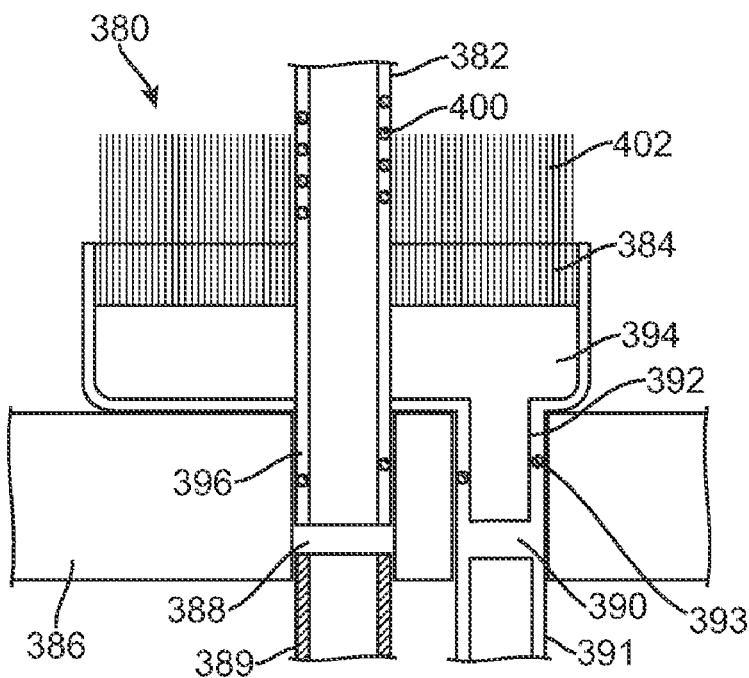
FIG. 13 is a detail cross-section view of another flow distribution arrangement for the membrane modules in the bank of FIG. 7.

FIGS. 12 & 13 illustrate flow distribution arrangements for membrane modules having intra-module ports in the potted end between the exterior of the membrane module and the inter-fiber space between the hollow fibers to communicate process gas to the inter-fiber space. In FIG. 12, the ports are the side tubes that feed gas into the intra-module area defined by the fibers through openings within the inter-fiber space. These openings may be supplied by hollow perforated support rods. In FIG. 13, the port is the perforated central support tube 382.

FIG. 12 is a detail cross-section view of a flow distribution arrangement for the membrane modules in the bank of FIG. 7. In this embodiment, the bottom plate 340 includes a gas distribution chamber 342 to provide gas to the membrane module 360. The bottom plate 340 includes a top plate 344 having a module opening 346, a support plate 348 having a liquid opening 350 in communication with a liquid branch line 351 and a gas opening 352 in communication with a gas branch line 353, and spacers 354 between the top plate 344 and the support plate 348 to maintain the distance between the plates 344, 348. The gas distribution chamber 342 is located between the top plate 344 and the support plate 348. The membrane module 360 includes an extension 362, a liquid chamber 364, a potted end 366 defining side tubes 368, 370, hollow fibers 372, gas seal flange 374, and support rods 376. A sealing element depicted by O-ring 363 prevents bypassing of liquid around extension 362. Support rods 376 connect the one potted end 366 of the membrane module 360 to the opposite potted end of the membrane module 360. The membrane module 360 rests on the support plate 348 and seals the distribution chamber 342 at the top plate 344 with the gas seal flange 374. Those skilled in the art will appreciate that suitable seals, such as an O-ring about the extension 362 or the like, can be provided between the membrane module 360 and the support plate 348 to separate the process liquid from the process gas. Process liquid flows through the liquid branch line 351, the extension 362, the liquid chamber 364, the potted end 366, and the hollow fiber lumens of the hollow fibers 372. Process gas flows through the gas branch line 353, the gas opening 352, the distribution chamber 342, the side tubes 368, 370, and between the hollow fibers 372. In one example, the side tube 368 opens into the inter-fiber space between the hollow fibers 372 at the potted end 366. In another example, the support rod 376 is hollow and perforated, and the side tube 370 opens into the hollow of the support rod 376. The process gas flows from the side tube 370, through the support rod 376, and into the intra-fiber space between the hollow fibers 372 along the support rod 376. Those skilled in the art will appreciate that the perforations in the support rod 376 can be arranged as desired for a particular application, such as at one end, both ends, or along the whole support rod. The gas seal flange 374 need not provide a perfect seal and can function mainly to provide enough pressure drop to maintain gas flow into the inter-fiber space.

FIG. 13 is a detail cross-section view of another flow distribution arrangement for the membrane modules in the bank of FIG. 7. In this embodiment, the membrane module 380 includes a perforated central support tube 382 to connect one potted end 384 of the membrane module 380 to the opposite potted end of the membrane module 380. The bottom plate 386 includes a gas opening 388 in communication with a gas branch line 389 and a liquid opening 390 in communication with a liquid branch line 391.

The membrane module 380 includes a liquid extension 392 in communication with a liquid chamber 394 and a gas extension 396, which can be part of the support tube 382. A sealing element depicted by O-ring 393 prevents bypassing of liquid around the liquid extension 392. The membrane module 380 rests on the bottom plate 386 with the liquid extension 392 received in the liquid opening 390 and the gas extension 396 received in the gas opening 388. Those skilled in the art will appreciate that suitable seals, such as O-rings about each of the liquid extension 392 and/or the gas extension 396 or the like, can be provided between the membrane module 380 and the bottom plate 386 to separate the process liquid from the process gas. The support tube 382 passes through the liquid chamber 394 and the potted end 384, and includes perforations 400 above the potted end 384 in the space between the hollow fibers 402. Process liquid flows through the liquid branch line 391, the liquid extension 392, the liquid chamber 394, and into the hollow fiber lumens of the hollow fibers 402 retained by potted end 384. Process gas flows through the gas branch line 389, into the support tube 382, and out the perforations 400 into the inter-fiber space between the hollow fibers 402. Those skilled in the art will appreciate that the perforations in the support tube 382 can be arranged as desired for a particular application, such as at one end, both ends, or along the whole support tube.

A bioreaction method includes retaining a process gas in a membrane vessel under anaerobic conditions; maintaining a plurality of membrane modules in a horizontally spaced arrangement and at least partially surrounded in the process gas, the membrane modules having a plurality of hollow fibers, each of the plurality of hollow fibers having a hollow fiber wall defining a hollow fiber lumen and an outer surface; growing a biolayer of microorganisms within biopores along the outer surface of the hollow fibers and producing a liquid product by interaction of the microorganisms with the process gas; and, passing a process liquid into the hollow fiber lumens and exchanging the process liquid through the hollow fiber wall to supply water and nutrients to biolayer and withdraw the liquid product in admixture with the process liquid. The biolayer can include microorganisms selected from the group consisting of *Clostridium ragsdalei, Butyribacterium methylotrophicum, Clostridium ljungdahlii, Clostridium carboxidivorans*, and combinations thereof. In one embodiment, the plurality of membrane modules are a two-headed membrane modules having a first potted end spaced apart from a second potted end, the first potted end is operably connected to one end of the hollow fibers and the second potted end is operably connected to the other end of the hollow fibers to allow the process liquid to flow through the hollow fiber lumens from the first potted end to the second potted end. The method can further include recovering the liquid product from the process liquid.

While the embodiments of the invention disclosed herein are presently considered to be preferred, various changes and modifications can be made without departing from the scope of the invention. For example, the direction of flow for the process gas and/or the process liquid can be up or down through the membrane modules, and can be concurrent or countercurrent. The scope of the invention is indicated in the appended claims, and all changes that come within the meaning and range of equivalents are intended to be embraced therein.

The invention claimed is:

1. A bioreaction method comprising:
retaining a process gas in a membrane vessel under anaerobic conditions;
maintaining a plurality of two-headed membrane modules in a horizontally spaced arrangement and at least partially surrounded in the process gas, the membrane modules having a plurality of hollow fibers, each of the plurality of hollow fibers having a hollow fiber wall defining a hollow fiber lumen and an outer surface, and having a first potted end spaced apart from a second potted end, the first potted end is operably connected to one end of the hollow fibers and the second potted end is operably connected to the other end of the hollow fibers to allow the process liquid to flow through the hollow fiber lumens from the first potted end to the second potted end;
growing a biolayer of microorganisms within biopores along the outer surface of the hollow fibers and producing a liquid product by interaction of the microorganisms with the process gas; and,
passing a process liquid into the hollow fiber lumens and exchanging the process liquid through the hollow fiber wall to supply water and nutrients to biolayer and withdraw the liquid product in admixture with the process liquid.

2. The method of claim 1 wherein the biolayer comprises microorganisms selected from the group consisting of *Clostridium ragsdalei, Butyribacterium methylotrophicum, Clostridium ljungdahlii, Clostridium carboxidivorans*, and combinations thereof.

3. The method of claim 1 further comprising recovering the liquid product from the process liquid.

4. The method of claim 1 wherein the hollow fiber wall comprises an asymmetric membrane wall having a porous layer about the outer surface that defines the biopores in which the biolayer grows and a less permeable hydration layer around the hollow fiber lumen.

* * * * *